US00PP31481P2

(12) United States Plant Patent
Van Swieten

(10) Patent No.: US PP31,481 P2
(45) Date of Patent: Feb. 25, 2020

(54) ***PHALAENOPSIS* ORCHID PLANT NAMED 'PHALFESFI'**

(50) Latin Name: ***Phalaenopsis* hybrid**
Varietal Denomination: PHALFESFI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,170

(22) Filed: Mar. 1, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

PUBLICATIONS

EU Community Plant Variety Rights Application No. 2018/1142, Application n°A201800763, filed Apr. 24, 2018, 8 pages.
EU Community Plant Variety Office Official Gazette, Mar. 2018, Jun. 15, 2018, cover page and pp. 35, 55.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALFESFI', particularly characterized by having white, striped flowers with reddish-purple centers and red-purple striped lips, 1 to 3 peduncles that are long and moderate, leaves that are oblong, and is propagated by meristem tissue culture, is disclosed.

3 Drawing Sheets

Genus and species: *Phalaenopsis* hybrid.
Variety denomination: 'PHALFESFI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFESFI'.

The new *Phalaenopsis* plant is a product of a planned breeding program conducted by the inventor in Bleiswijk, The Netherlands. The objective of this breeding program was to create a new *Phalaenopsis* plant with numerous attractive white, striped flowers with reddish-purple centers and red-purple striped lips, suitable for potted plant production.

The new *Phalaenopsis* plant 'PHALFESFI' is a result of cross-pollination made by the inventor in January 2006 in Bleiswijk, The Netherlands, of the proprietary female, or seed parent, *Phalaenopsis* hybrid '23390-04' (unpatented) with the proprietary male, or pollen parent, *Phalaenopsis* hybrid 'PHALBUKALO' (U.S. Plant Pat. No. PP28,322).

The new *Phalaenopsis* was selected by the inventor as a single plant within the progeny of the stated cross-pollination in a controlled greenhouse in Bleiswijk, The Netherlands, in November 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2018, by Applicant who obtained the subject matter disclosed directly from the Inventor. 'PHALFESFI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALFESFI' as a new and distinct variety of *Phalaenopsis* plant:

1) White, striped flowers with reddish-purple centers and red-purple striped lips;
2) 1 to 3 peduncles;
3) Peduncle is long and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week-old plants in January 2019. Colors in the photographs may differ from the color values cited in the detailed botanical description, which accurately describe the actual colors of the new variety.

DESCRIPTION OF THE NEW VARIETY

Figure 1:
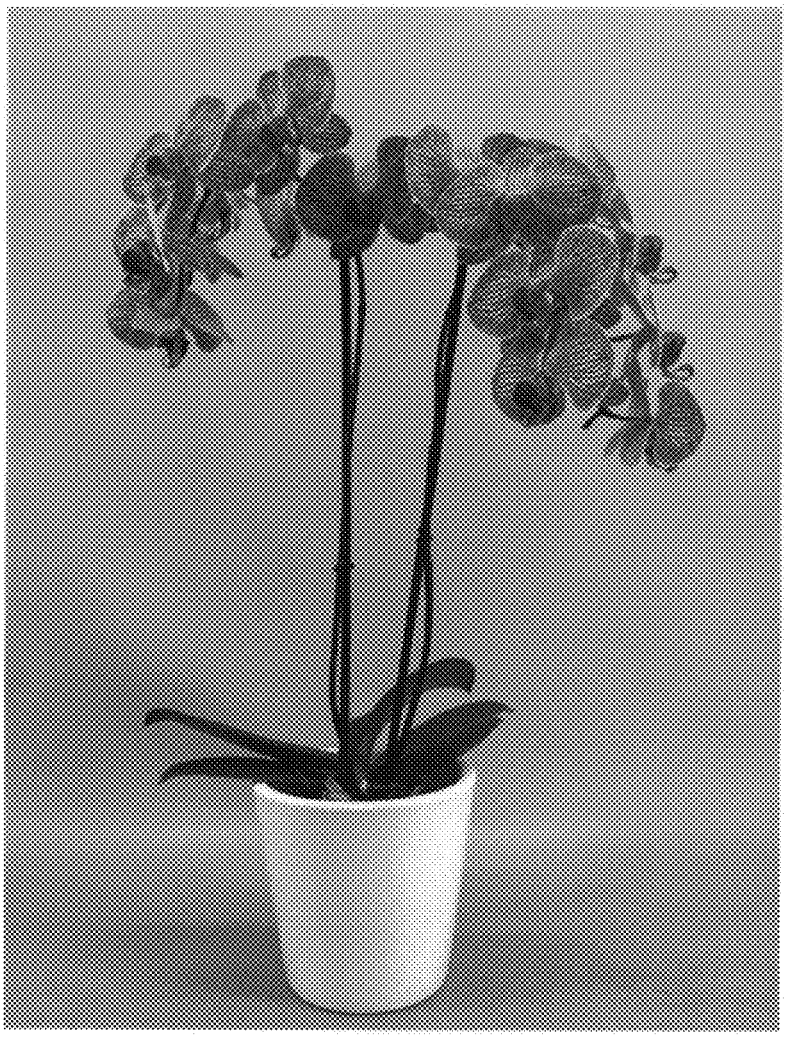
FIG. 1 shows the overall plant habit, including blooms and foliage of 'PHALFESFI'.
Figure 2:
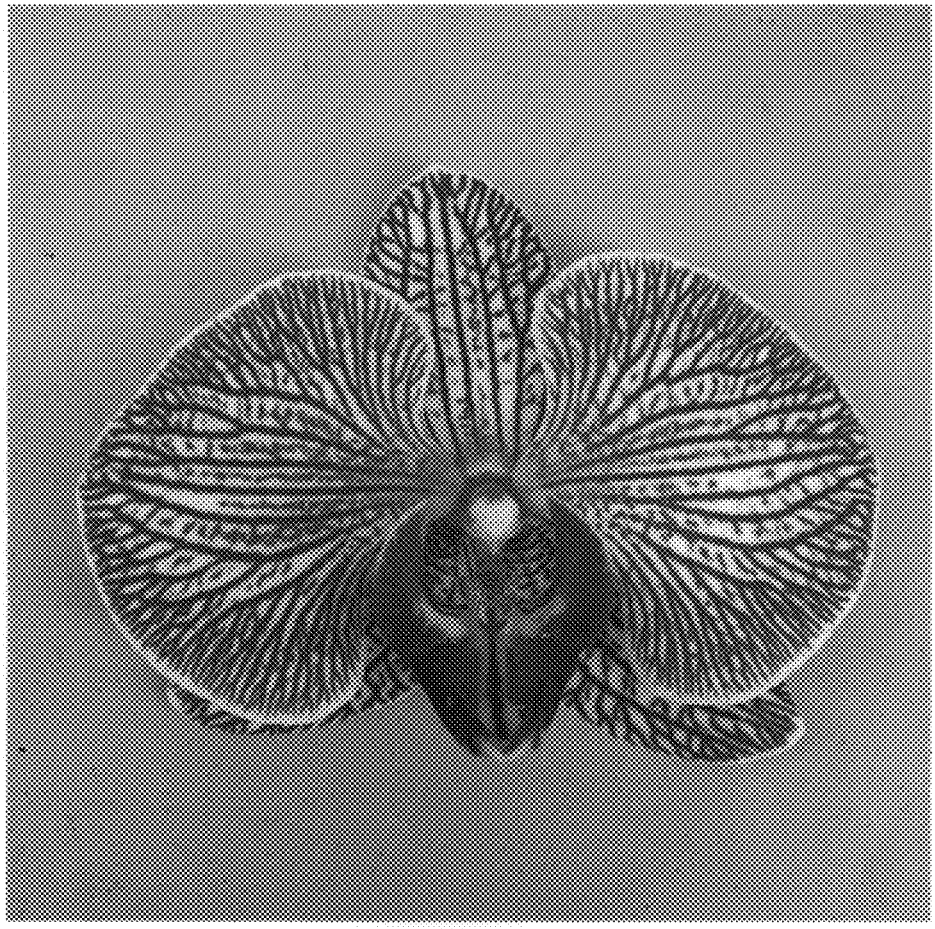
FIG. 2 shows a close-up of a flower of 'PHALFESFI'.
Figure 3:
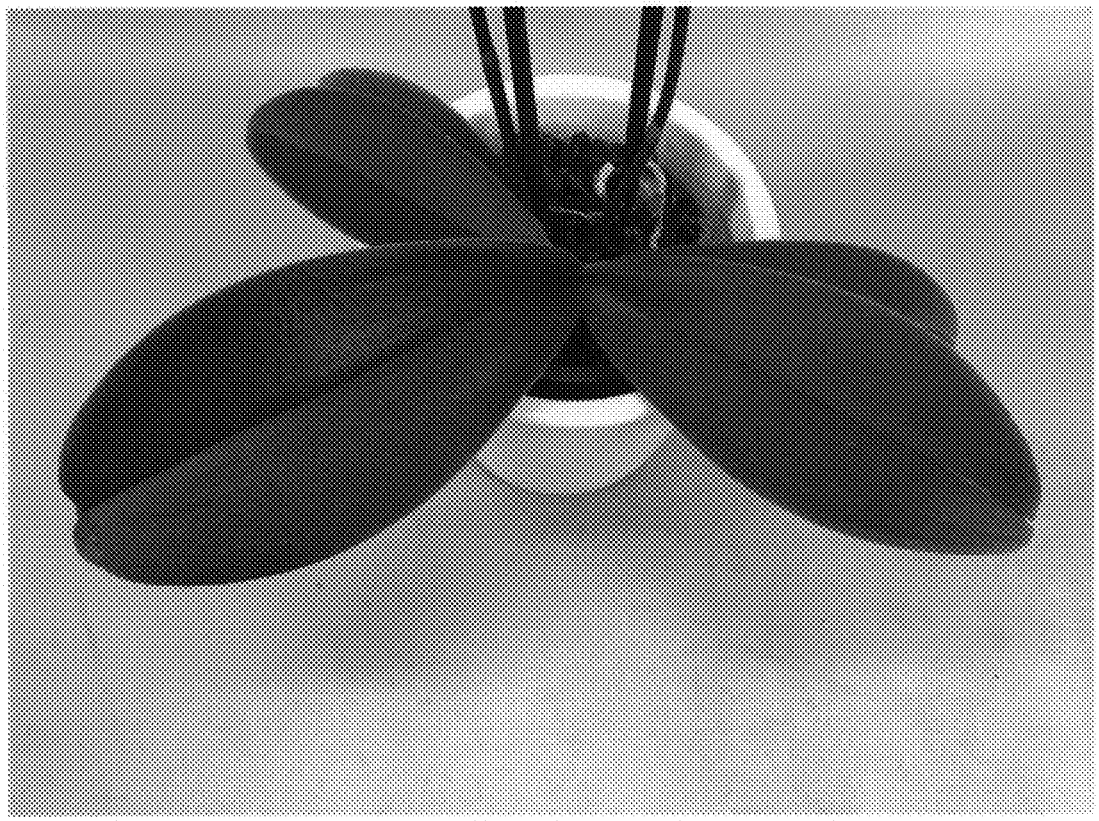
FIG. 3 shows an overhead view of the leaves of 'PHALFESFI'.

The following detailed description sets forth the distinctive characteristics of 'PHALFESFI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALFESFI'.

Parentage:

*Female parent.*—*Phalaenopsis* cultivar '23390-04' (unpatented).

*Male parent.*—*Phalaenopsis* cultivar 'PHALBUKALO' (U.S. Plant Pat. No. 28,322).

Propagation:

*Type.*—Meristem tissue culture.

Roots:

*Root description.*—Greyed-green (between RHS 190B and 190C) colored roots with branching lateral roots having light yellow-green (RHS 145D) colored root tips.

Plant:

*Commercial crop time to flowering.*—Following asexual propagation (in-vitro), the rooted cuttings grow for 20-24 weeks. After transplantation into 12-cm pots, the plants are finished after 48 to 50 weeks.

*Growth habit of peduncle.*—Upright to slightly pendant with raceme inflorescence.

*Height (from soil level to top of inflorescence).*—Approximately 55.0 cm to 60.0 cm.

*Width (measured from leaf tips).*—About 33.0 cm to 35.0 cm.

*Vigor.*—Moderate.

Leaves:

*Mature leaves.*—Quantity per plant: 7 to 8 leaves are produced before flowering. Length (fully expanded): 15.0 cm to 17.0 cm. Width: 8.0 cm to 9.0 cm. Shape: Oblong. Base shape: Moderately elongated. Apex: Obtuse unequal. Leaf blade angle with the petiole (measured from the horizontal position): Between 15 degrees and 25 degrees. Leaf margin: Entire. Color: Upper surface: RHS 146A. Lower surface: RHS 146B. Texture (upper surface): Rough. Texture (lower surface): Slightly rough. Thickness: 2.5 mm to 2.9 mm. Venation: Pattern: Parallel. Color of the midvein: Upper surface: RHS 146A. Lower surface: RHS 146B.

Peduncle:

*Quantity per plant.*—1 to 3.

*Number of flowers per peduncle.*—8 to 12.

*Length.*—51.0 cm to 56.0 cm.

*Diameter.*—4.4 mm to 4.7 mm.

*Strength.*—Strong.

*Aspect.*—Upright to slightly pendant.

*Texture.*—Smooth.

*Color.*—Mix of yellow-green (RHS 146C) and brown (RHS N200A).

*Internode length.*—4.0 cm to 5.0 cm.

Inflorescence description:

*Appearance.*—Upright to slightly pendant, raceme inflorescence with bilaterally symmetrical flowers that open in succession beginning with the lowermost flower.

*Inflorescence size.*—Height (from base to tip): 180.0 mm to 210.0 mm. Diameter: 120.0 mm to 140.0 mm.

*Flowering time.*—First flowers can be expected 10 to 11 months after planting in a 12-cm pot.

*Flower.*—Height: 65.0 mm to 70.0 mm. Diameter: 82.0 mm to 87.0 mm. Depth of lip: 22.0 mm to 24.0 mm.

*Flower longevity.*—On the plant: 8 to 14 weeks.

*Fragrance.*—Absent.

*Flower bud.*—Average size: Large. Length: 23.0 mm to 25.0 mm. Width: 19.0 mm to 21.0 mm. Shape: Egg shaped. Color: Mix of yellow-green (RHS 195B) and purplish-red (RHS N77B).

*Petals.*—Arrangement: Open/free. Shape: Semi-circular. Apex: Obtuse asymmetric. Margin: Entire. Length (from base to tip): 38.0 mm to 40.0 mm. Width: 49.0 mm to 51.0 mm. Color (when fully opened): Upper surface: Basic color: White (RHS NN155C). Over color: Red-purple stripes (RHS N78A) and shade (RHS N78B). Lower surface: Basic color: Very light purple (RHS 76C). Over color: Red-purple stripes (between RHS N78B and N78C).

*Dorsal sepal.*—Shape: Elliptic. Apex: Obtuse symmetric. Margin: Entire. Length (from base to tip): 40.0 mm to 42.0 mm. Width: 25.0 mm to 27.0 mm. Color (when fully opened): Upper surface: Basic color: White (RHS NN155C). Over color: Reddish-purple (RHS N78B) at the base and reddish-purple stripes (RHS N78A). Lower surface: Basic color: Light purple (RHS 76A). Over color: Purplish-pink (RHS N78C); diluting reddish-purple stripes (RHS N78A) toward margin; slightly yellow-green (RHS 195B) toward the tip.

*Lateral sepals.*—Shape: Ovate. Apex: Obtuse asymmetric. Margin: Entire. Length (from base to tip): 40.0 mm to 42.0 mm. Width: 22.0 mm to 24.0 mm. Color (when fully opened): Upper surface: Basic color: White (RHS NN155C). Over color: Light yellow-green (RHS 145D) at the base; reddish-purple stripes and spots (RHS N78A). Lower surface: Basic color: Light purple (RHS 76A). Over color: Yellow-green (between RHS 195A and 195B) at the base and diluting reddish-purple stripes (RHS N78B).

*Labellum* (*lip*).—Whiskers: Present. Length of whiskers: 15.0 mm to 17.0 mm. Color of whiskers: Dark red (RHS 187B) and dark purplish-red (RHS N79C). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Undulated. Length: 16.0 mm to 18.0 mm. Width: 13.0 mm to 15.0 mm. Color: Upper surface: Slightly white (RHS NN155C) and yellow (RHS 13B). with dark red stripes (RHS 59A) at the base; red (RHS 185A) on one side and reddish-purple (RHS N78B) toward the other side with dark red-purplish stripes (RHS N79B) toward the edge. Lower surface: White (RHS NN155C); yellow (RHS 13C) on one side; reddish-purple stripes (RHS N78A) and region (RHS N78B) toward the margin.

*Apical lobe.*—Shape: Triangular. Margin: Entire. Length: 21.0 mm to 23.0 mm. Width: 20.0 mm to 22.0 mm. Color: Upper surface: Slightly yellow (RHS 13C) at the base with red wings (RHS 185A); dark purplish-red (RHS N79C) toward the whiskers and white region (RHS NN155C) in the middle. Lower surface: Slightly purplish-red (RHS N77B) at the base; white (RHS NN155C) in the middle; reddish-orange wings (RHS 176C); reddish-purple stripes and region (RHS N78A) toward margin; dark purplish-red (RHS N79C) toward whiskers.

*Callus.*—Average size: Medium. Height: 5.0 mm to 6.0 mm. Length: 5.0 mm to 6.0 mm. Width: 3.0 mm to 4.0 mm. Color: Yellow (RHS 13B); dotted (RHS 59A).

Reproductive organs:

*Column.*—Length: 9.0 mm to 11.0 mm. Diameter: 4.7 mm to 5.2 mm. Color: Light reddish-purple (RHS N78D) with reddish-purple region (RHS N78B) toward the tip.

*Pollinia.*—Quantity: 2. Diameter: 0.9 mm to 1.1 mm. Color: Orange (RHS 24A).

*Ovary.*—Length: 8.0 mm to 10.0 mm. Diameter: 1.9 mm to 2.2 mm. Color: Light yellow-green (RHS 195C) and light reddish-purple (RHS N78D) toward the flower.

*Pedicel.*—Length: 30.0 mm to 32.0 mm. Diameter: 2.3 mm to 2.5 mm. Color: Dark purplish (RHS N79B) at the base; mix of yellow-green (RHS 195B and 195C) and light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFESFI' differs from female parent plant '23390-04' (unpatented) in that 'PHALFESFI' has dark red and dark purplish-red whiskers with white tips, and light reddish-purple (RHS N78D) columns with reddish-purple region (RHS N78B) toward the tip, whereas '23390-04' has dark red whiskers with yellow tips, and light purple (RHS 76A) columns. Additionally, 'PHALFESFI' has smaller flowers than '23390-04'.

'PHALFESFI' differs from male parent plant 'PHALBUKALO' (U.S. Plant Pat. No. 28,322) in that 'PHALFESFI' has obtuse asymmetric petal apexes, whereas 'PHALBUKALO' has slightly emarginated asymmetric petal apexes. Additionally, 'PHALFESFI' has narrower dorsal sepals than 'PHALBUKALO'.

'PHALFESFI' is most similar to the commercial *Phalaenopsis* plants named 'PHALBUKAP' (U.S. Plant Pat. No. 25,445) and 'PHALCTOZYP' (U.S. Plant Pat. No. 27,670). 'PHALFESFI' differs from the commercial variety 'PHALBUKAP' in that 'PHALFESFI' has obtuse asymmetric petal apexes, and oblong leaves with obtuse unequal apexes, whereas 'PHALBUKAP' has mucronate symmetric petal apexes, and narrow obovate leaves with mucronate apexes. Additionally, 'PHALFESFI' has shorter whiskers than 'PHALBUKAP'.

'PHALFESFI' differs from the commercial variety 'PHALCTOZYP' in that 'PHALFESFI' has obtuse asymmetric petal apexes, and dark red (RHS 187B) and dark purplish-red (RHS N79C) whiskers with white tips, whereas 'PHALCTOZYP' has rounded asymmetric petal apexes, and dark red (RHS 59A) whiskers with yellow edges and tips. Additionally, 'PHALFESFI' has longer whiskers than 'PHALCTOZYP'.

I claim:

1. A new and distinct variety of *Phalaenopsis* plant named 'PHALFESFI', substantially as described and illustrated herein.

* * * * *